US012661112B2

(12) United States Patent
Sonoda et al.

(10) Patent No.: US 12,661,112 B2
(45) Date of Patent: Jun. 23, 2026

(54) SURGICAL DEVICE RETRACTING MECHANISM

(71) Applicant: RIVERFIELD INC., Tokyo (JP)

(72) Inventors: Koh-hei Sonoda, Fukuoka City (JP); Shintaro Nakao, Fukuoka (JP); Kotaro Tadano, Tokyo (JP); Tatsuhito Fukuda, Tokyo (JP)

(73) Assignee: RIVERFIELD INC., Tokyo (JP)

( * ) Notice: Subject to any disclaimer, the term of this patent is extended or adjusted under 35 U.S.C. 154(b) by 681 days.

(21) Appl. No.: 17/990,138

(22) Filed: Nov. 18, 2022

(65) Prior Publication Data

US 2023/0078683 A1      Mar. 16, 2023

Related U.S. Application Data

(63) Continuation of application No. PCT/JP2020/020201, filed on May 21, 2020.

(51) Int. Cl.
A61B 34/30 (2016.01)
A61B 17/072 (2006.01)

(52) U.S. Cl.
CPC ........ A61B 17/07207 (2013.01); A61B 34/30 (2016.02)

(58) Field of Classification Search
CPC .......... A61B 17/07207; A61B 17/3403; A61B 2017/3409; A61B 2090/508; A61B 34/30; A61B 90/50
See application file for complete search history.

(56) References Cited

U.S. PATENT DOCUMENTS

| | | | |
|---|---|---|---|
| 5,195,961 | A | 3/1993 | Takahashi et al. |
| 6,107,581 | A | 8/2000 | Tanigawa et al. |
| 9,855,396 | B2 | 1/2018 | Topping et al. |
| 10,226,379 | B2 | 3/2019 | Oberkircher et al. |
| 2012/0211006 | A1 | 8/2012 | Gill et al. |
| 2013/0338577 | A1 | 12/2013 | Al-Habaibeh et al. |
| 2015/0342695 | A1 | 12/2015 | He et al. |

FOREIGN PATENT DOCUMENTS

| | | |
|---|---|---|
| JP | 02-034166 A | 2/1990 |
| JP | 11-232953 A | 8/1999 |
| JP | 2014-514016 A | 6/2014 |
| JP | 2019-147052 A | 9/2019 |
| WO | 2018/101265 A1 | 6/2018 |
| WO | 2020/081434 A1 | 4/2020 |

OTHER PUBLICATIONS

Shintaro Kimura et al., "Development of Intraocular Endoscope Manipulator", Proceedings of JSME Annual Conference on Robotics and Mechatronics (Robomec), The Japan Society of Mechanical Engineers, 2018, 3 pages.
International Search Report of PCT/JP2020/020201 dated Aug. 25, 2020 [PCT/ISA/210].
Extended European Search Report dated May 23, 2023, issued in European Application No. 20936340.7.

*Primary Examiner* — Deborah L Malamud
(74) *Attorney, Agent, or Firm* — Sughrue Mion, PLLC

(57) ABSTRACT

A surgical device retracting mechanism includes a holder that holds a surgical device, a guide that guides the holder to linearly advance and retract, a locking member that locks the holder in a locking state in which the surgical device is inserted in a surgical site, and a retracting device that releases the locking state and retract the holder based on a detection signal.

17 Claims, 2 Drawing Sheets

SURGICAL DEVICE RETRACTING MECHANISM

CROSS REFERENCE TO RELATED APPLICATIONS

This application is a continuation application of International Patent Application No. PCT/JP2020/020201 filed on May 21, 2020, the contents of which is incorporated by reference herein in its entirety.

BACKGROUND

1. Field

The present disclosure relates to a technology for quickly retracing a surgical device such as forceps or an endoscope from a surgical site.

2. Description of Related Art

Medical treatments using robots (manipulators) have recently been proposed in order to reduce the burden on operators and save manpower in medical facilities. In the field of surgery, proposals have been made for surgical manipulator systems for operators to treat patients by operating remotely-controllable surgical manipulators.

For example, an intraocular endoscope manipulator robot may insert an endoscope into an eyeball of a patient. However, since the intraocular endoscope manipulator robot retracts the endoscope by moving an arm, a direction in which the endoscope is retracted from the eyeball is not linear, and a load is thus applied to the eyeball during retraction.

SUMMARY

It is an aspect to provide a novel technology for reducing a load applied to a surgical site while a surgical device is retracted from the surgical site.

According to an aspect of one or more embodiments, there is provided a surgical device retracting mechanism comprising a holder configured to hold a surgical device; a guiding member configured to guide the holder to linearly advance and retract; a locking member configured to lock the holder in a locking state in which the surgical device is inserted in a surgical site; and a retracting device configured to release the locking state of the locking member and retract the holder in accordance with a signal from outside the retracting device.

According to another aspect of one or more embodiments, there is provided a surgical device retracting mechanism comprising a holder configured to hold a surgical device; a guide that guides the holder to linearly advance and retract; a locking member configured to lock the holder in a locked state in which the surgical device is inserted in a surgical site; and a retracting device configured to release the locked state and retract the holder based on a detection signal.

According to yet another aspect of one or more embodiments, there is provided a surgical apparatus comprising a holder configured to hold a surgical device; a linear guide that guides the holder; a tension spring having a first end attached to an end of the holder and a second end attached to an end of the linear guide; a rod configured to rotate about a fulcrum, the rod having a first end that contacts the holder and a second end that is biased by a solenoid to lock the holder in a locked state in which the surgical device does not move along the linear guide when the surgical device is inserted in a surgical site; a compression spring attached to the second end of the rod and providing a force opposite to a bias force generated by the solenoid, wherein, based on a detection signal, the solenoid releases the second end to release the locked state such that the holder moves to retract the surgical device from the surgical site along the linear guide.

BRIEF DESCRIPTION OF THE DRAWINGS

The above and/or other aspects will become apparent and more readily appreciated from the following description of various embodiments, taken in conjunction with the accompanying drawings, in which.

DETAILED DESCRIPTION

Figure 1:
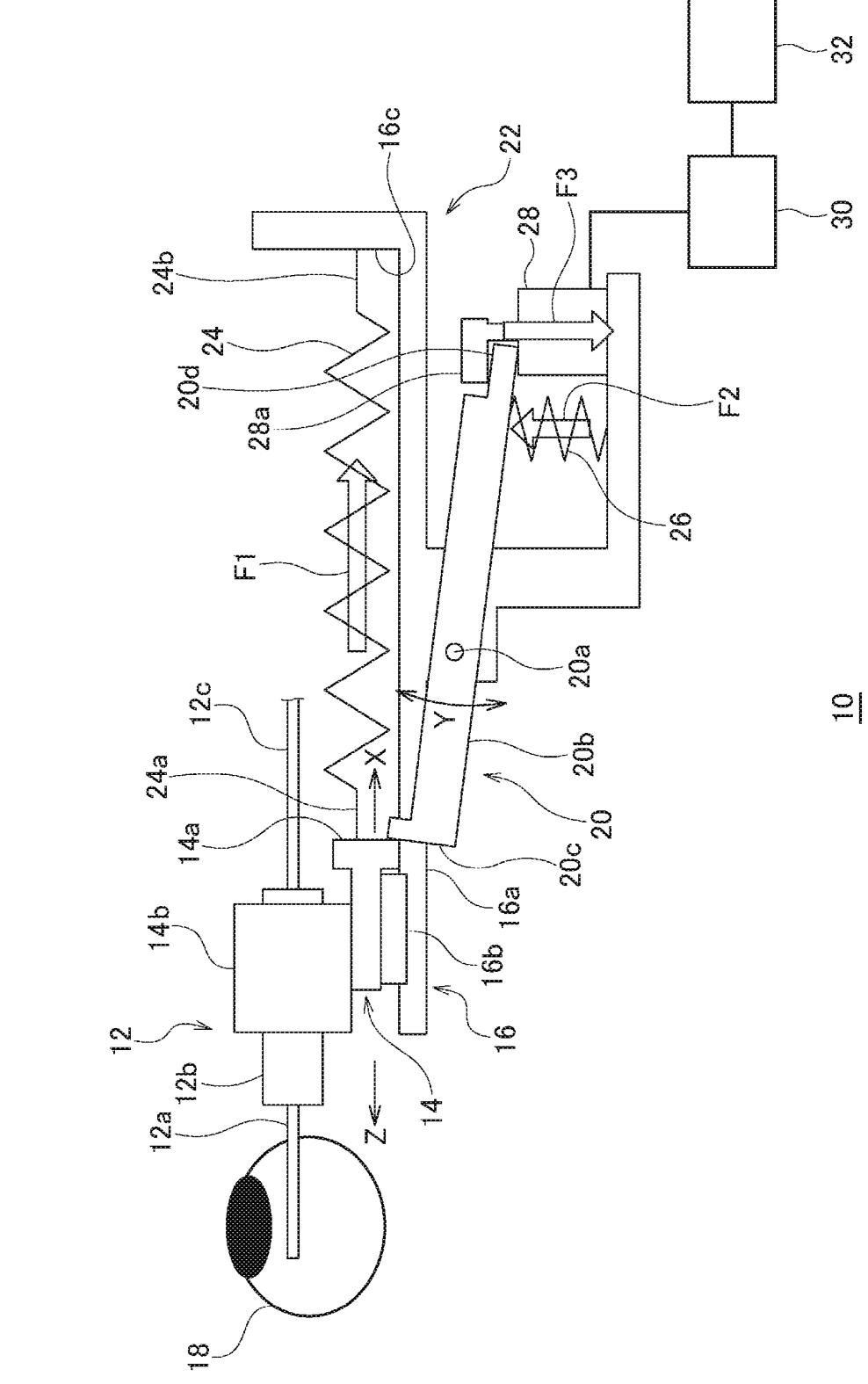
FIG. 1 is a side view illustrating an outline structure of a surgical device retracting mechanism in a state in which an endoscope is inserted into an eyeball by the surgical device retracting mechanism, according to some embodiments.

Various embodiments will now be described with reference to the drawings. Components, members, and processes that are the same as or equivalent to each other illustrated in the drawings are represented by the same reference numerals, and redundant explanation will not be repeated where appropriate for conciseness. The various embodiments are merely examples, and any feature or any combination of features described in the embodiments is not necessarily essential.

In the related art, an intraocular endoscope manipulator robot may insert an endoscope into an eyeball in a state in which a brake of an arm is off so that joints of the arm with three degrees of freedom of the arm become passive, and once the endoscope is inserted, the intraocular endoscope manipulator robot may apply the brake. Because an eyeball of a patient may move during an operation on the eyeball, the aforementioned manipulator robot includes a mechanism for disabling the brake when the patient moves so that the joints become passive, and for retracting the endoscope from the eyeball by the arm returning to a predetermined position.

As discussed above, because the robot retracts the endoscope by moving the arm, the direction in which the endoscope is retracted from the eyeball is not linear, and a load is thus applied to the eyeball during retraction.

It is an aspect to provide a novel technology for reducing a load applied to a surgical site while a surgical device is retracted from the surgical site.

A surgical device retracting mechanism according to some embodiments may include a holder for holding a surgical device; a guiding member for guiding the holder to linearly advance and retract; a locking member for locking the holder in a state in which the surgical device is inserted in a surgical site; and a retracting device for releasing a locking state of the locking member and retracting the holder in accordance with a signal from outside the retracting device.

This configuration and operation allows a surgical device linearly inserted into a surgical site along the guiding member to be retracted in parallel with the inserting direction of the surgical device. As a result, the load applied to the surgical site during retraction of the surgical device is reduced.

According to some embodiments, the retracting device may include a first force generating member for generating a first force in a retracting direction of the holder in a state in which the holder is locked; a second force generating member for generating a second force for releasing the locking state of the locking member; and a third force generating member for maintaining the locking state of the locking member against the second force. This configuration and operation achieves holding and retraction of a surgical device by adjusting the forces generated by the respective force generating members by a simple structure.

According to some embodiments, the locking member may be a turnable member that is turnable about a fulcrum, and the turnable member may have a first end coming in contact with the holder and a second end on which the third force acts in the locking state. This configuration and operation allows the third force generating member for generating the third force to be placed at a position away from the holder, which increases the flexibility of layout of respective components without making the structure complicated.

According to some embodiments, the second force generating member may be a compression spring, and the third force generating member may be a pull-type solenoid for pulling the second end of the turnable member while power supply to the pull-type solenoid is on. In some embodiments, the second force generating member may be a tension spring, and the third force generating member may be a push-type solenoid for pushing the second end of the turnable member while power supply to the push-type solenoid is on. With this configuration and operation, in such an emergency in which power supply to the pull-type solenoid or the push-type solenoid is cut off owing to a power failure or a device failure, for example, the surgical device is quickly retracted from the surgical site without requiring special control.

According to some embodiments, the compression spring of the retracting device may have a spring constant set so that the locking state of the locking member is released while power supply to the pull-type solenoid is off. This configuration and operation allows generation of the second force by the restoring force of the compression spring without using power.

According to some embodiments, the first force generating member may be a tension spring. This configuration allows generation of the first force by the restoring force of the tension spring without using power.

The surgical device held by the holder may be an endoscope to be inserted into an eyeball. This configuration and operation allows an endoscope inserted in such a soft and delicate surgical site as an eyeball to be quickly retracted in an emergency while reducing the load applied to the eyeball.

According to some embodiments, a sensor for detecting a movement of an eyeball or a movement of a head may further be included. According to some embodiments, the retracting device may be configured to release the locking state of the locking member in accordance with a signal in response to the movement of the eyeball or the movement of the head detected by the sensor. This configuration and operation allows the endoscope held in a state inserted in an eyeball to be quickly retracted before a great load is applied to the eyeball by the movement of the position of the eyeball.

A method, a device, a system, and the like consistent with the above description may also be provided.

According to various embodiments, the load applied to a surgical site when a surgical device is retracted from the surgical site is reduced.

Figure 2:
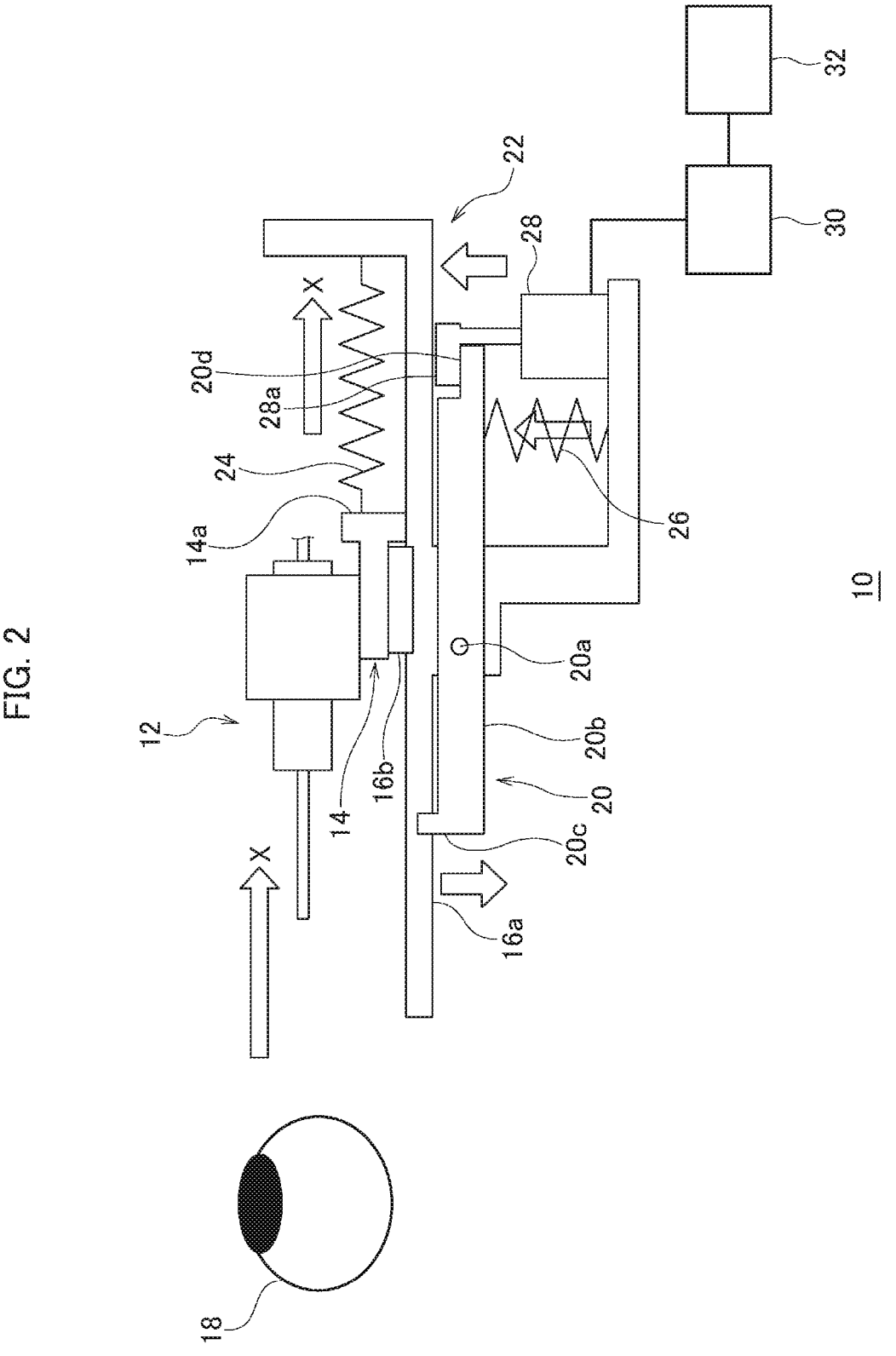
FIG. 2 is a side view illustrating the outline structure in a state in which the endoscope is retracted from the eyeball by the surgical device retracting mechanism, according to some embodiments.

FIG. 1 is a side view illustrating an outline structure of a surgical device retracting mechanism in a state in which an endoscope is inserted into an eyeball by the surgical device retracting mechanism according to some embodiments. FIG. 2 is a side view illustrating an outline structure of the surgical device retracting mechanism in a state in which the endoscope is retracted from the eyeball by the surgical device retracting mechanism according to some embodiments.

A surgical device retracting mechanism 10 illustrated in FIG. 1 includes a holder 14 for holding a surgical device 12, a guiding member 16 for guiding the holder 14 to linearly advance and retract, a locking member 20 for locking the position of the holder 14 in a state in which the surgical device 12 is inserted in an eyeball 18, which is a surgical site, and a retracting device 22 for releasing the locking state of the locking member 20 and retracting the holder 14 in accordance with a signal from outside. In some cases, the surgical device 12 may also be referred to as a surgical tool or a surgical instrument. In some embodiments, the surgical device 12 may be an endoscope or a forceps.

The surgical device 12 includes a fiber-like insertion portion 12a having a diameter of about 0.5 to 1.2 mm to be inserted into an eyeball 18, and a grip 12b, a cable 12c. The grip 12b is held by an adapter 14b of the holder 14. The guiding member 16 includes a linear guide 16a, and a stage 16b configured to slide along the linear guide 16a.

The retracting device 22 includes a tension spring 24 that is a first force generating member for generating a first force F1 in a direction X in which the holder 14 is to be retracted in a state in which the holder 14 is locked, a compression spring 26 that is a second force generating member for generating a second force F2 for releasing the locking state of the locking member 20, and a pull-type solenoid 28 that is a third force generating member for generating a third force F3 for maintaining, against the second force F2, the locking state of the locking member 20.

A first end 24a of the tension spring 24 is fixed to an end 14a in the retracting direction of the holder 14. A second end 24b of the tension spring 24 is fixed to an end 16c of the linear guide 16a. The locking member 20 is a rod-like turnable member 20b configured to turn about a fulcrum 20a in a Y direction. The turnable member 20b has a first end 20c that comes in contact with the end 14a of the holder 14 and a second end 20d on which the third force F3 acts in the locking state.

The pull-type solenoid 28 pulls the second end 20d of the turnable member 20b while power is on. Specifically, the pull-type solenoid 28 has a hook-like catching portion 28a at an end of a plunger thereof. The catching portion 28a fixes the second end 20d of the turnable member 20b in a state in which the second end 20d is pulled downward.

The compression spring 26 of the retracting device 22 according to some embodiments has a spring constant and a length set so that the locking state of the locking member 20 is released while the pull-type solenoid 28 is powered off. In addition, the retracting device 22 further includes a controller 30 for controlling power supply to the pull-type solenoid 28, and a sensor 32 for detecting the movement of an eyeball 18 and/or the movement of a head. In some embodiments, the controller may be, for example, a processor or hardware control logic configured to control power supply to the pull-type solenoid 28 based on a detection signal from the sensor 32 that indicates indicating that the movement of the eyeball 18 and/or the movement of the head is detected by the sensor 32. In some embodiments, the processor may be a central processing unit (CPU), a microprocessor, or a microcontroller.

Next, an operation of immediately retracting the surgical device 12 from an eyeball 18 in an X direction will be explained with reference to FIG. 2. As illustrated in FIG. 2, when the pull-type solenoid 28 is powered off, the third force F3 by which the catching portion 28a of the pull-type solenoid 28 has pulled the second end 20d of the turnable member 20b downward is eliminated. As a result, the second end 20d is pushed upward and the first end 20c, which is located on a side opposite the second end 20d with respect to the fulcrum 20a, is pushed downward by the restoring force of the compression spring 26, and the locking of the holder 14 by the locking member 20 is thus released.

As a result, the restoring force of the tension spring 24 with the first end 24a fixed to the end 14a of the holder 14 moves the holder 14 in the X direction, and the surgical device 12 is retracted from the eyeball 18 in the X direction.

As described above, the surgical device retracting mechanism 10 according to some embodiments allows the surgical device 12 linearly inserted into an eyeball 18 that is the surgical site along the linear guide 16a to be retracted in parallel (in the X direction) with the inserting direction Z of the surgical device 12. As a result, the load applied to the eyeball 18 while the surgical device 12 is retracted from the eyeball 18 is reduced.

In addition, the surgical device retracting mechanism 10 achieves holding and retraction of the surgical device 12 by adjusting the forces generated by the tension spring 24, the compression spring 26, and the pull-type solenoid 28 by a simple structure.

In addition, in the surgical device retracting mechanism 10, because the pull-type solenoid 28 that requires power supply and a relatively large space may be placed at a position away from the holder 14, the flexibility of layout of respective components is increased without making the structure complicated.

Furthermore, in an emergency in which power supply to the pull-type solenoid 28 is cut off owing to a power failure or a device failure, for example, the surgical device retracting mechanism 10 is capable of quickly retracting the surgical device 12 from an eyeball 18 without requiring special control. In addition, the surgical device retracting mechanism 10 is capable of generating the second force F2 by the restoring force of the compression spring 26 without using power, and similarly capable of generating the first force F1 by the restoring force of the tension spring 24 without using power.

Furthermore, the surgical device retracting mechanism 10 is capable of quickly retracting the surgical device 12 inserted in such a soft and delicate surgical site as the eyeball 18 in an emergency while reducing the load applied to the eyeball 18.

In addition, the control device 30 of the retracting device 22 according to some embodiments is configured to release the locking state of the locking member 20 by controlling current to turn off power supply to the pull-type solenoid 28 in accordance with a signal in response to a movement of the eyeball or the like detected by the sensor 32. This allows the surgical device 12 held in a state inserted in the eyeball 18 to be quickly retracted before a large load is applied to the eyeball 18 by the movement of the position of the eyeball 18.

While the retracting device 22 according to some embodiments is a combination of the compression spring 26, which is the second force generating member, and the pull-type solenoid 28, which is the third force generating member, a retracting device may be configured as a combination of a tension spring, as a second force generating member, for pulling the turnable member 20b upward and a push-type solenoid, as a third force generating member, for pushing the second end 20d of the turnable member 20b downward when power is supplied to the push-type solenoid.

While various embodiments have been described above with reference to the drawings, embodiments are not limited thereto, and any combination or substitution of components as appropriate is included in the present disclosure. In addition, modifications such as combinations, changes in the order of processes, and various changes in design may be made on the basis of knowledge of a person skilled in the art, and such modified embodiments are within the scope of the present disclosure and appended claims.

The present disclosure is applicable to a technology for quickly retracting a surgical device such as a forceps or an endoscope from a surgical site.

It should be understood that embodiments are not limited to the various embodiments described above, but various other changes and modifications may be made therein without departing from the spirit and scope thereof as set forth in appended claims.

What is claimed is:

1. A surgical device retracting mechanism comprising:
a holder configured to hold a surgical device;
a guiding member configured to guide the holder to linearly advance and retract;
a locking member configured to lock the holder in a locking state in which the surgical device is inserted in a surgical site; and
a retracting device configured to release the locking state of the locking member and retract the holder in accordance with a signal from outside the retracting device, wherein
the retracting device includes:
a first force generating member that generates a first force in a retracting direction of the holder in the locking state in which the holder is locked;
a second force generating member that generates a second force for releasing the locking state of the locking member; and
a third force generating member that maintains the locking state of the locking member against the second force,
the locking member is a turnable member that is turnable about a fulcrum, and
the turnable member has a first end that contacts with the holder and a second end on which the third force acts in the locking state.

2. The surgical device retracting mechanism according to claim 1, wherein:
the second force generating member is a compression spring, and
the third force generating member is a pull-type solenoid for pulling the second end of the turnable member while power supply to the pull-type solenoid is on.

3. The surgical device retracting mechanism according to claim 2, wherein:
the compression spring of the retracting device has a spring constant such that the locking state of the locking member is released while power supply to the pull-type solenoid is off.

4. The surgical device retracting mechanism according to claim 1, wherein the first force generating member is a tension spring.

5. The surgical device retracting mechanism according to claim 1, wherein the surgical device held by the holder is an endoscope configured to be inserted into an eyeball of a patient.

6. The surgical device retracting mechanism according to claim 1, further comprising:

a sensor that detects a movement of an eyeball or a movement of a head and outputs the signal, wherein the retracting device is configured to release the locking state of the locking member in accordance with the signal in response to the movement of the eyeball or the movement of the head detected by the sensor.

7. A surgical device retracting mechanism comprising:

a holder configured to hold a surgical device;

a guide that guides the holder to linearly advance and retract;

a locking member configured to lock the holder in a locked state in which the surgical device is inserted in a surgical site; and a retracting device configured to release the locked state and retract the holder based on a detection signal, wherein the retracting device includes:

a tension spring that generates a first force in a retracting direction of the holder in the locked state;

a compression spring that generates a second force for releasing the locked state; and a solenoid that maintains the locked state against the second force.

8. The surgical device retracting mechanism according to claim 7, wherein:

the locking member comprises a rod that is rotatable about a fulcrum, and a first end of the rod contacts the holder in the locked state; and the third force acts on a second end of the rod in the locked state.

9. The surgical device retracting mechanism according to claim 8, wherein the solenoid pulls the second end of the rod while power is supplied to the solenoid.

10. The surgical device retracting mechanism according to claim 9, wherein:

a spring constant of the compression spring is such that the locked state is released while power is not supplied to the solenoid.

11. The surgical device retracting mechanism according to claim 7, wherein the surgical device comprises an endoscope and the surgical site comprises an eyeball of a patient.

12. The surgical device retracting mechanism according to claim 7, further comprising:

a sensor that detects a movement of an eyeball and/or a movement of a head and outputs the detection signal when movement of the eyeball and/or movement of the head is detected.

13. A surgical apparatus comprising:

a holder configured to hold a surgical device;

a linear guide that guides the holder;

a tension spring having a first end attached to an end of the holder and a second end attached to an end of the linear guide;

a rod configured to rotate about a fulcrum, the rod having a first end that contacts the holder and a second end that is biased by a solenoid to lock the holder in a locked state in which the surgical device does not move along the linear guide when the surgical device is inserted in a surgical site;

a compression spring attached to the second end of the rod and providing a force opposite to a bias force generated by the solenoid, wherein, based on a detection signal, the solenoid releases the second end to release the locked state such that the holder moves to retract the surgical device from the surgical site along the linear guide.

14. The surgical apparatus according to claim 13, wherein the solenoid pulls the second end of the rod while power is supplied to the solenoid.

15. The surgical apparatus according to claim 13, wherein the solenoid releases the second end of the rod while power is not supplied to the solenoid.

16. The surgical apparatus according to claim 13, wherein the surgical device comprises an endoscope and the surgical site comprises an eyeball of a patient.

17. The surgical apparatus according to claim 16, further comprising:

a sensor that detects a movement of the eyeball and/or a movement of a head of the patient and outputs the detection signal when movement of the eyeball and/or movement of the head is detected.

\* \* \* \* \*